(12) United States Patent
Steinberger et al.

(10) Patent No.: US 11,992,660 B2
(45) Date of Patent: May 28, 2024

(54) NEEDLELESS INJECTION DEVICE EQUIPPED WITH AN IMPROVED INJECTION NOZZLE

(71) Applicant: CROSSJECT, Dijon (FR)

(72) Inventors: Robin Steinberger, Leobersdorf (AT); Gilles Vivien, Malakof (FR)

(73) Assignee: CROSSJECT, Dijon (FR)

( * ) Notice: Subject to any disclaimer, the term of this patent is extended or adjusted under 35 U.S.C. 154(b) by 779 days.

(21) Appl. No.: 16/126,167

(22) Filed: Sep. 10, 2018

(65) Prior Publication Data

US 2019/0001063 A1   Jan. 3, 2019

Related U.S. Application Data

(63) Continuation of application No. PCT/FR2017/050321, filed on Feb. 13, 2017.

(30) Foreign Application Priority Data

Mar. 8, 2016   (FR) ...................................... 16/51928

(51) Int. Cl.
*A61M 5/30*   (2006.01)

(52) U.S. Cl.
CPC ............ *A61M 5/3007* (2013.01); *A61M 5/30* (2013.01); *A61M 2205/0216* (2013.01)

(58) Field of Classification Search
CPC .................. A61M 5/30; A61M 5/3007; A61M 2205/0216; A61M 2005/3132
See application file for complete search history.

(56) References Cited

U.S. PATENT DOCUMENTS

| | | | |
|---|---|---|---|
| 2,650,591 A | * | 9/1953 | Love ...................... A61M 5/30 222/327 |
| 2,667,874 A | | 2/1954 | Dickinson, Jr. |

(Continued)

FOREIGN PATENT DOCUMENTS

| | | |
|---|---|---|
| FR | 2815544 | 4/2002 |
| FR | 2853837 | 10/2004 |

(Continued)

OTHER PUBLICATIONS

The American Society of Mechanical Engineers, ASME B1.1 Unified Inch Screw Threads, 1989, p. 3 (Year: 1989).*

(Continued)

*Primary Examiner* — Courtney B Fredrickson
(74) *Attorney, Agent, or Firm* — Burris Law, PLLC

(57) ABSTRACT

A needleless injection device includes a body forming a receptacle extending axially from an upper radial seat along an injection axis, a gas generator, a tubular reservoir containing an active ingredient and extending axially in the receptacle from an upper end to a lower end, and a nozzle for injecting the active ingredient. The nozzle is arranged at the lower end of the reservoir and has an outer thread to be screwed onto a complementary thread formed by the body. The external thread of the nozzle has an overall triangular cross-section and is delimited by an upper face, which has a first angle with respect to a radial axis perpendicular to the injection axis, and a lower face, which has a second angle with respect to the radial axis. The first angle is greater than the second angle.

10 Claims, 2 Drawing Sheets

(56) References Cited

U.S. PATENT DOCUMENTS

| | | | |
|---|---|---|---|
| 3,802,430 A * | 4/1974 | Schwebel | A61M 5/30 604/69 |
| 5,061,135 A | 10/1991 | Pritchard | |
| 5,875,976 A * | 3/1999 | Nelson | A61M 5/30 239/600 |
| 7,150,409 B2 * | 12/2006 | Gonnelli | A61M 5/30 239/320 |
| 9,648,908 B1 * | 5/2017 | Rinehart | A24F 40/40 |
| 2002/0123717 A1 | 9/2002 | Landau | |
| 2003/0097093 A1 * | 5/2003 | Navelier | A61M 5/30 604/68 |
| 2004/0015125 A1 * | 1/2004 | Alexandre | A61M 5/30 604/69 |
| 2004/0069044 A1 * | 4/2004 | Lavi | A61M 5/19 604/93.01 |
| 2004/0249339 A1 | 12/2004 | Willis et al. | |
| 2006/0089595 A1 * | 4/2006 | Alexandre | A61M 5/30 604/69 |
| 2006/0189927 A1 * | 8/2006 | Alexandre | A61M 5/30 604/72 |
| 2011/0176889 A1 | 7/2011 | Olsen et al. | |
| 2012/0203184 A1 * | 8/2012 | Selz | A61M 5/3156 604/189 |
| 2015/0050102 A1 | 2/2015 | Lu | |

FOREIGN PATENT DOCUMENTS

| | | | |
|---|---|---|---|
| JP | 2001507963 | 6/2001 | |
| JP | 2002126082 | 5/2002 | |
| JP | 5732039 B2 * | 6/2015 | A61P 29/00 |
| WO | 1997031665 | 9/1997 | |
| WO | 1998028030 | 7/1998 | |
| WO | WO-0207803 A1 * | 1/2002 | A61M 5/3015 |
| WO | 2010108116 | 9/2010 | |
| WO | 2012044259 | 4/2012 | |
| WO | 2014200066 | 12/2014 | |

OTHER PUBLICATIONS

Bouche, Dipl.-Ing. Ch., et al., Dubbels Taschenbuch fuer den Maschinenbau, Springer-Verlag Berlin Heidelberg GmbH, 1953, pp. 602-605.

International Search Report for international application PCT/FR2017/050321, mailed Apr. 4, 2017.

* cited by examiner

NEEDLELESS INJECTION DEVICE EQUIPPED WITH AN IMPROVED INJECTION NOZZLE

CROSS-REFERENCE TO RELATED APPLICATIONS

This application is a continuation of International Application No. PCT/FR2017/050321, filed on Feb. 13, 2017, which claims priority to and the benefit of FR 16/51928 filed on Mar. 8, 2016. The disclosures of the above applications are incorporated herein by reference.

FIELD

The present disclosure relates to a needleless injection device equipped with an improved injection nozzle.

BACKGROUND

The statements in this section merely provide background information related to the present disclosure and may not constitute prior art.

The technical field of the present disclosure is that of the needleless, pre-filled and disposable injection devices, operating with an energy source such as for example a gas generator, and used for the intradermal, subcutaneous and intramuscular injections of liquid active ingredient for therapeutic use in human or veterinary medicine.

The active ingredient is constituted by a more or less viscous liquid, a mixture of liquid, or a gel. The active ingredient may also be a solid dissolved in a solvent suitable for the injection or be constituted of a powdery solid suspended at a certain concentration in a suitable liquid. The particle size of the active ingredient must then be compatible with the diameter of the ducts to avoid sealing them.

An injection device includes, in a known manner, as for example in the patent application FR-A-2815544 (equivalent to WO 02/34317), a body successively comprising a gas generator, an expansion chamber, a reservoir containing the liquid active ingredient and an injection system.

The reservoir is constituted by a glass tube which is inserted into a tubular housing delimited by the body of the device, the tube being sealed by an upper or upstream piston and a lower or downstream piston, between which the liquid active ingredient is contained.

The free lower end of the reservoir cooperates with an injection nozzle which delimits at least one injection channel extending axially along an injection axis.

Furthermore, the injection device includes a hollow cover which wraps the body and which delimits a lower opening adapted for the passage of the injection nozzle.

In order to allow the injection of the active ingredient, the body is slidably mounted in the cover, from bottom to top along a sliding axis, between a rest position and an injection position, the driving of the body being carried out when the user presses the injection nozzle on his skin.

The displacement of the body in the cover allows the triggering of the gas generator, generating a pressurized gas which drives the pistons in displacement to inject the active ingredient through the skin of the patient, by passing through the injection nozzle.

There is known an injection device which is equipped with a generally T-shaped elastically deformable membrane, which comprises a radial annular disc which is axially interposed between the upper end of the reservoir and a seat formed by the body, and a tubular portion which extends axially in the reservoir, from the annular disc.

The tubular portion of the membrane is designed to extend axially under the effect of the pressurized gas, in order to drive the pistons in displacement.

The injection nozzle is axially delimited by an upper face axially bearing on the reservoir, and a lower injection face adapted to cooperate with a closure cap.

Also, the injection nozzle has an external thread adapted to be screwed onto a complementary tapping formed by the body.

Thus, the screwing of the nozzle on the body allows axially pinching the radial annular disc of the membrane between the upper end of the reservoir and the seat formed by the body, in order to ensure the sealing between the membrane, the reservoir and the body during the injection.

Under the effect of the pressure generated by the gas generator, a sliding between the body and the assembly formed by the membrane and the reservoir is sometimes observed.

This sliding partially disengages the connection between the membrane and the body until creating more or less significant leakages randomly disturbing the injection features of the injection device, these leakages generating dispersions on the injection performances.

SUMMARY

The present disclosure relates to a needleless injection device including:
  a body forming a housing which extends axially from an upper radial seat, along an injection axis;
  a gas generator;
  a tubular reservoir which contains an active ingredient and which extends axially in said housing from an upper end, to a lower end; and
  a nozzle for injecting the active ingredient which is arranged at the lower end of the reservoir, and which has an external thread adapted to be screwed onto a complementary tapping formed by the body, the injection device being characterized in that the thread of the nozzle has a generally triangular section, said thread being delimited by an upper face which has a first angle relative to a radial axis perpendicular to the injection axis, and a lower face which has a second angle relative to said radial axis, and in that the first angle is greater than the second angle.

The design of the nozzle according to the present disclosure allows limiting the second angle formed by the lower face of the thread of the nozzle, which allows a larger tightening torque of the nozzle before rupture of the nozzle or of the complementary tapping formed by the body.

Thus, the risk of leakage between the membrane and the reservoir is reduced.

According to another feature, the thread is of the sawtooth type, that is to say the second angle formed by the lower face of the nozzle is non-zero such that said lower face forms a flank face.

Such a flank face promotes the demolding of the nozzle during its manufacture.

In one form, the first angle is of about 35 degrees.

Also, the second angle is of about 10 degrees. An angle of 10 degrees is an interesting compromise which simultaneously promotes the demolding of the nozzle and which allows a large tightening torque of the nozzle.

According to another feature, the lower face of the thread of the nozzle bears on a complementary upper face of the associated tapping formed by the body, to resume the axial thrust forces transmitted by the nozzle during the injection.

Also, the curved portion which connects two adjacent triangles formed by the thread 72 has a radius of curvature of about 0.11 millimeter.

Furthermore, the pitch of the thread is of about one millimeter.

In one form, the injection nozzle is made by injection molding.

Similarly, the body is made by injection molding.

According to another feature, the active ingredient contained in the reservoir is selected from the following active ingredients:

Methotrexate,
Adrenaline,
Sumatriptan,
Hydrocortisone,
Naloxone,
Midazolam,
Apomorphine,
Ethylnatrexone bromide,
Phytomenadione,
Chlorpromazine hydrochloride,
Zuclopenthixol acetate,
Danaparoid sodium,
Enoxaparin sodium,
Estradiol cypionate,
Medoxyprogesterone acetate,
Medroparin calcium,
Methylprednisolone acetate,
Heparin calcium, and
Terbulin.

Further areas of applicability will become apparent from the description provided herein. It should be understood that the description and specific examples are intended for purposes of illustration only and are not intended to limit the scope of the present disclosure.

DRAWINGS

In order that the disclosure may be well understood, there will now be described various forms thereof, given by way of example, reference being made to the accompanying drawings, in which.

Figure 1:
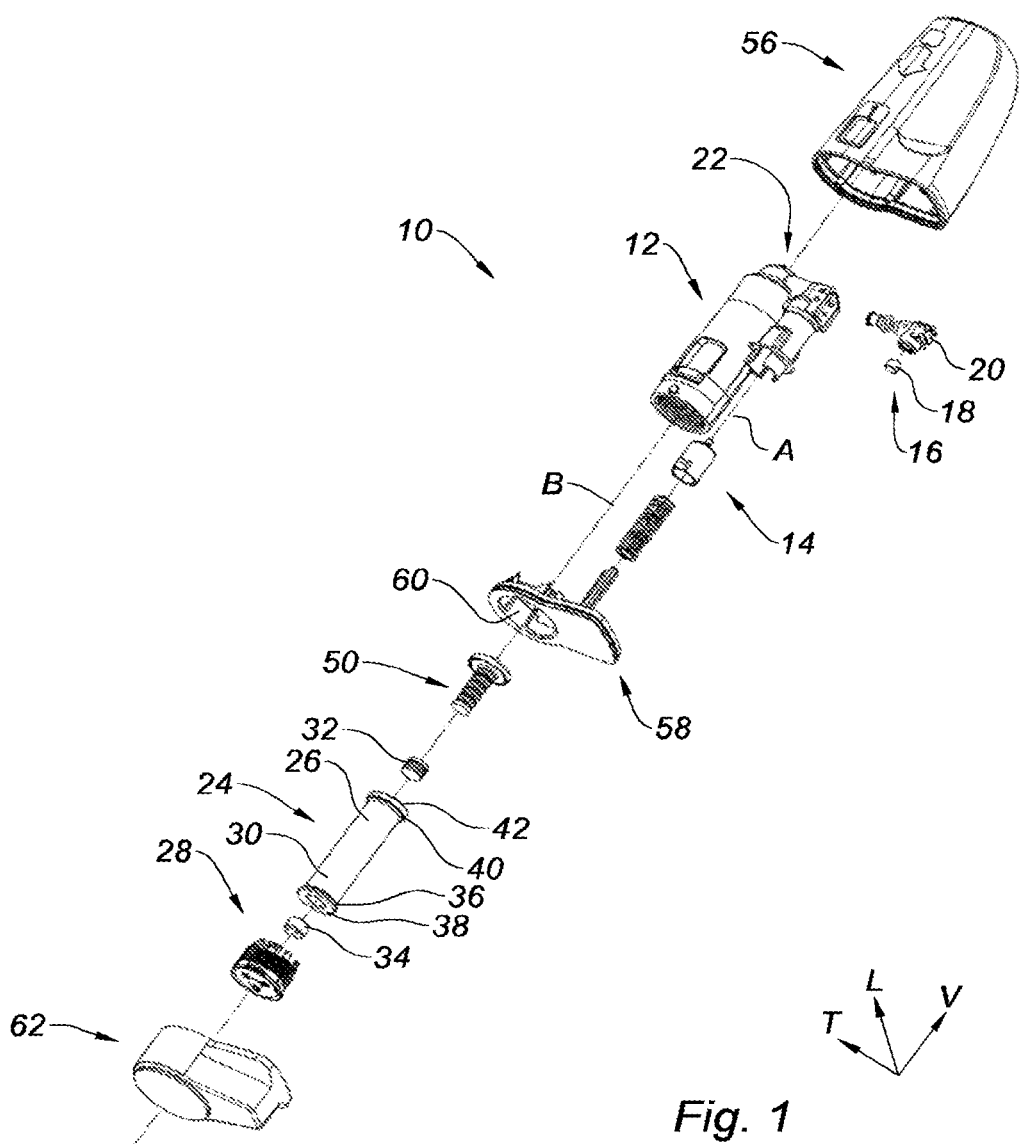
FIG. 1 is an exploded perspective view which illustrates an injection device according to the present disclosure.

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features.

In the present disclosure, in order to clarify the description and claims, the longitudinal, vertical and transverse terminology will be adopted in a non-limiting way with reference to the trihedron L, V, T indicated in the Figures.

Furthermore, in the present application, the terms "upper," "lower," "horizontal," "vertical," and their derivatives refer to the position or the orientation of an element or a component, this position or this orientation being considered with reference to the orientation of the device in the Figures and to the trihedron L, V, T, without reference to earth's gravity.

Similarly, the terms "axial" and "radial" should be understood with reference to the injection axis B of the injection device.

FIG. 1 shows a needleless injection device, or needleless syringe, which includes a U-shaped body 12 successively comprising a percussion device 14, a gas generator 16 comprising a primer 18 and a pyrotechnic charge 20, an expansion chamber 22, a reservoir 24 containing the liquid active ingredient 26 and an injection nozzle 28.

The percussion device 14 and the gas generator 16 constitute a first linear subassembly of the body 12 which extends axially along a vertical sliding axis A, and the reservoir 24 containing the active ingredient 26 and the injection nozzle 28 form a second linear subassembly of the body 12 which extends axially along a second vertical injection axis B.

These two subassemblies are connected to each other by the expansion chamber 22 which has an axis perpendicular to the axes A, B of the subassemblies.

The reservoir 24 is constituted by a glass tube 30 sealed by an upper piston 32 and a lower piston 34 between which the liquid active ingredient 26 is contained, the pistons being made of an elastically deformable elastomer-based material.

The reservoir 24 extends axially from a lower flange 36 which has an annular lower face 38 arranged facing the injection nozzle 28, to an upper flange 40 having an annular upper face 42.

Figure 2:
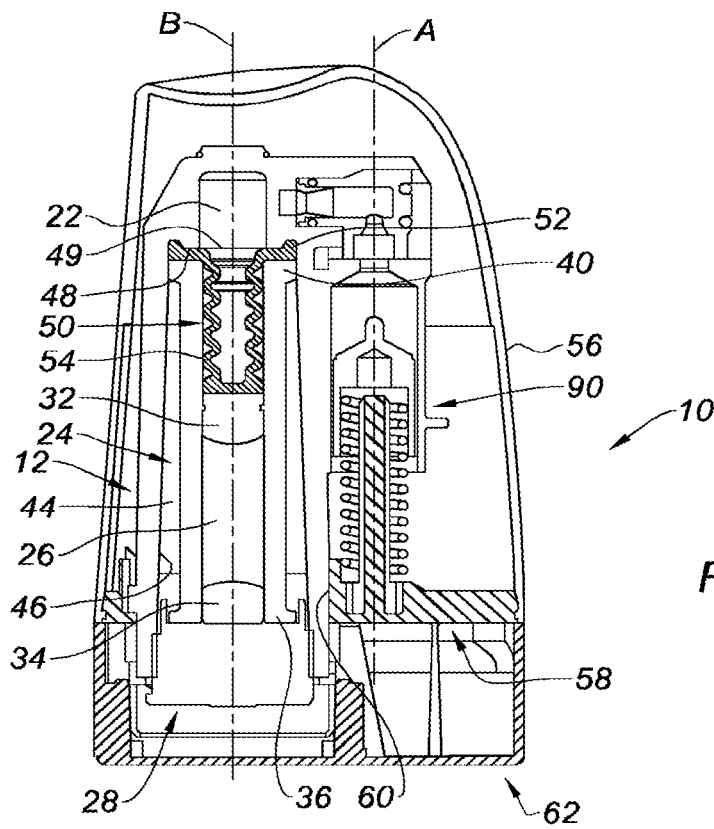
FIG. 2 is an axial cross-sectional view which illustrates the device of FIG. 1 in a rest position.

As seen in FIG. 2, the reservoir 24 is arranged in a housing 44 formed by the body 12, housing 44 which is delimited radially by a tubular wall 46 which extends about the injection axis B.

The housing 44 extends axially from an upper radial seat 48 which is formed by the body 12 and which delimits an outlet orifice 49 of the expansion chamber 22.

According to one form, the body 12 is made by plastic injection molding.

Also, according to FIG. 2, the device 10 is equipped with a generally T-shaped elastically deformable membrane 50, which comprises a radial annular disc 52 which is interposed axially between the upper flange 40 of the reservoir 24 and the seat 48 formed by the body 12, and a tubular portion 54 which extends axially in the reservoir 24, from the annular disk 52.

The tubular portion 54 of the membrane 50 is designed to extend axially, under the effect of the pressure of the gas generated by the gas generator 16, to push the upper piston 32 downwards in order to eject the active ingredient 26 through the injection nozzle 28.

To this end, the membrane 50 is made of an elastomer-based material. More particularly, the membrane 50 is made of EPDM, that is to say of ethylene-propylene-diene monomer.

With reference to FIG. 1, the body 12 is wrapped by a hollow cover 56 which delimits a lower opening closed by a horizontal soleplate 58 forming a bottom of the cover.

The soleplate 58 delimits a circular passage 60 about the injection axis B which is adapted for the passage of the injection nozzle 28 and the lower end of the body 12, such that the nozzle 28 includes a lower segment protruding vertically downwards out of the cover 56.

Also, the injection device 10 is equipped with a plug 62 which is removably mounted on the body 12 by a bayonet-type locking device.

The nozzle 28 is screwed onto a free end emerging from the housing 44 formed by the body 12, the nozzle 28 compressing axially the assembly formed by the reservoir 24 and the membrane 50 on the seat 48 of the housing 44.

Figure 3:
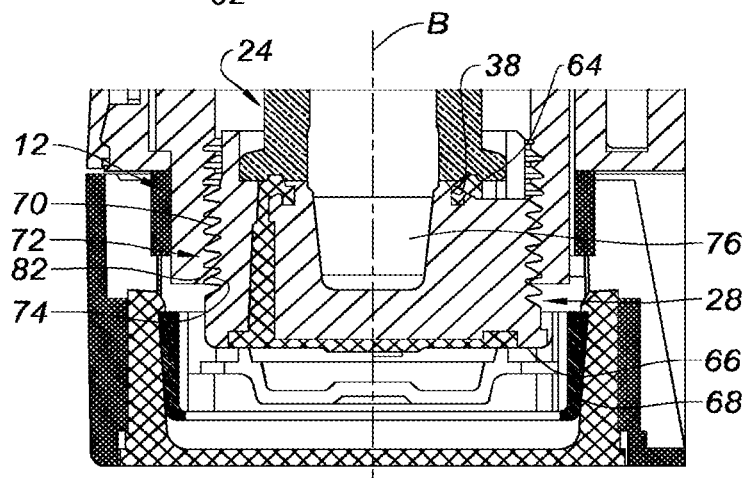
FIG. 3 is a detailed axial cross-sectional view which illustrates the coupling of the injection nozzle on the body of the injection device of FIG. 1.

Also, the injection nozzle 28, illustrated in detail in FIG. 3, has a generally cylindrical shape which extends axially along the injection axis B from an upper face axially bearing on the lower face 38 of the reservoir 24, to a lower injection face adapted to cooperate with a closure cap 68.

The cylindrical peripheral face 70 of the nozzle 28 has a thread 72 designed to screw the nozzle 28 on the free end of the body 12, the body 12 being equipped with a complementary tapping 74 provided for this purpose.

Furthermore, the nozzle 28 delimits three axial injection channels (not shown) which extend parallel to the injection axis B, each channel opening into the upper face 64 and into the lower face 66 of the nozzle 28.

The nozzle 28 delimits a central housing 76 which is adapted to receive the lower piston 34 following the triggering of the injection.

More particularly, the free upper end of each channel forms a flaring which communicates with the housing 76, so as to allow the active ingredient 26 to enter each channel, from the housing, when the lower piston 34 has fallen into the housing 76.

Indeed, when the gas generator 16 is triggered, the pressurized gas pushes the liquid column formed by the upper piston 32, the active ingredient 26 and the lower piston 34, the lower piston 34 falling into the housing 76 of the nozzle 28 provided to this end in order to allow the active ingredient 26 to flow through the channels.

Figure 4:
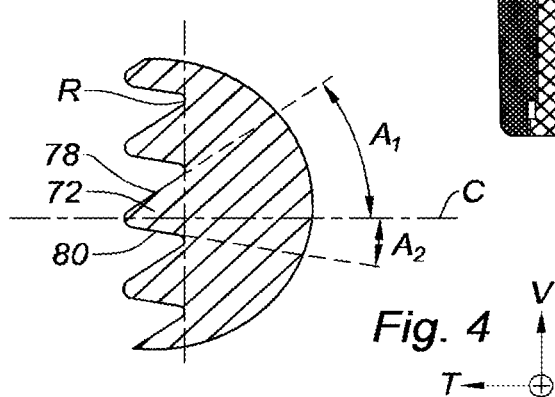
FIG. 4 is a detailed axial cross-sectional view of a pullout which illustrates the thread of the nozzle of FIG. 3.

In accordance with the present disclosure, with reference to FIG. 4, the thread 72 of the nozzle 28 has a generally triangular section, the thread 72 being delimited by an upper face 78 which has a first angle A1 relative to a transverse radial axis C perpendicular to the injection axis B, and a lower face 80 which has a second angle A2 relative to the radial axis C.

As seen in FIG. 4, the first angle A1 is greater than the second angle A2.

The thread 72 of the nozzle 28 is of the sawtooth type, that is to say the second angle A2 formed by the lower face 80 of the nozzle 28 is non-zero such that the lower face 80 forms a flank face.

Indeed, the injection nozzle 28 is made by plastic injection molding and the lower face 80 forms a flank face allowing the demolding of the nozzle 28 from its manufacturing mold.

More particularly, the first angle A1 is of about 35 degrees and the second angle A2 is of about 10 degrees.

Thus, the angle delimited between the upper face 78 and the lower face 80 of the thread 72 is of about 45 degrees.

According to FIG. 3, the lower face 80 of the thread 72 of the nozzle 28 bears on a complementary upper face 82 of the associated tapping 74 formed by the body 12, to resume the axial thrust forces transmitted by the nozzle 28 during the injection.

According to one form, the curved portion R which connects two adjacent triangles formed by the thread 72 has a radius of curvature of about 0.11 millimeter. The term curved portion R means the recessed portion which connects the lower face 80 of a first triangle and the upper face 78 of a second triangle adjacent to the thread 72 of the nozzle 28.

Also, the pitch of the thread 72 is of about one millimeter.

The injection device 10 according to the present disclosure has several advantages.

Due to the sawtooth shape of the thread 72, the forces transmitted on the body 12 are close to the vertical, more particularly these forces are perpendicular to the lower face 80 of the thread 72 forming a bearing face, that is to say the forces are close to an angle of 10 degrees relative to a vertical axis.

Conversely, according to the related art, the thread 72 is generally a metric thread, or isometric thread, that is to say a thread in equilateral triangle section which is delimited by an upper face which has a first angle close to thirty degrees, and a lower face which has a second angle also close to thirty degrees.

Thus, the device 10 according to the present disclosure allows less basing the body 12 by radial forces, in order to avoid breaking the body 12.

Furthermore, the device according to the present disclosure allows a large tightening torque of the nozzle 28 on the body 12, which allows axially compressing sufficiently the annular disk 52 of the membrane 50 against the seat 48 formed by the body 12, in order to avoid the leakages at this level.

The description of the disclosure is merely exemplary in nature and, thus, variations that do not depart from the substance of the disclosure are intended to be within the scope of the disclosure. Such variations are not to be regarded as a departure from the spirit and scope of the disclosure.

What is claimed is:

1. A needleless injection device comprising:
a body forming a housing extending axially in a direction of injection from an upper radial seat of the housing along an injection axis;
a gas generator;
a tubular reservoir containing an active ingredient and a lower piston disposed below the active ingredient, the tubular reservoir extending axially in said housing from an upper end of the tubular reservoir to a lower end of the tubular reservoir;
an upper piston having an upper axial surface; and
a nozzle for injecting the active ingredient which is arranged at the lower end of the tubular reservoir and which extends axially in the direction of injection from the lower end of the tubular reservoir, the nozzle including an external thread adapted to be screwed onto a complementary tapping formed by the body such that the nozzle is configured to axially compress the reservoir on the upper radial seat of the housing and a central housing adapted to receive the lower piston, the external thread extending axially in the direction of injection from the lower end of the tubular reservoir to a position beyond the lower end the tubular reservoir and extending around the central housing,
wherein the external thread of the nozzle includes a triangular section, said external thread being delimited by an upper face having a first angle relative to a radial axis perpendicular to the injection axis and a lower face having a second angle relative to said radial axis, wherein the first angle is greater than the second angle, and
wherein an elastically deformable membrane extends axially in the reservoir and is configured to expel the active ingredient from the reservoir, the elastically deformable membrane has an accordion shape and a lower surface that abuts against the upper axial surface of the upper piston, the elastically deformable membrane further comprises an annular disc interposed axially between the upper end of the reservoir and the upper radial seat of the housing.

2. The needleless injection device according to claim 1, wherein the thread is sawtooth shaped and the second angle formed by the lower face of the nozzle is non-zero such that said lower face forms a flank face.

3. The needleless injection device according to claim 1, wherein the first angle is about 35 degrees.

4. The needleless injection device according to claim 1, wherein the second angle is about 10 degrees.

5. The needleless injection device according to claim 1, wherein the lower face of the thread of the nozzle bears on a complementary upper face of the tapping formed by the body and is arranged to distribute axial thrust forces from the lower piston to the complementary upper face of the tapping during injection.

6. The needleless injection device according to claim 1, wherein a curved portion that connects two adjacent triangles formed by the thread has a radius of curvature of about 0.11 millimeter.

7. The needleless injection device according to claim 1, wherein a pitch of the thread is about one millimeter.

8. The needleless injection device according to claim 1, wherein the nozzle is made by injection molding.

9. The needleless injection device according to claim 1, wherein the body is made by injection molding.

10. The needleless injection device according to claim 1, wherein the active ingredient contained in the tubular reservoir is selected from the group consisting of Methotrexate, Adrenaline, Sumatriptan, Hydrocortisone, Naloxone, Midazolam, Apomorphine, Ethylnatrexone bromide, Phytomenadione, Chlorpromazine hydrochloride, Zuclopenthixol acetate, Danaparoid sodium, Enoxaparin sodium, Estradiol cypionate, Medoxyprogesterone acetate, Medroparin calcium, Methylprednisolone acetate, Heparin calcium, and Terbulin.

* * * * *